United States Patent [19]

Harandi et al.

[11] Patent Number: 4,885,421
[45] Date of Patent: Dec. 5, 1989

[54] MULTISTAGE REACTOR SYSTEM FOR PRODUCTION OF FUELS

[76] Inventors: Mohsen N. Harandi, 12 Catbord Ct., Lawrenceville, N.J. 08648; Hartley Owen, 5 Riverview Ter., Belle Mead, N.J. 08502

[21] Appl. No.: 271,836

[22] Filed: Nov. 16, 1988

Related U.S. Application Data

[63] Continuation-in-part of Ser. No. 130,256, Dec. 8, 1987, Pat. No. 4,788,365.

[51] Int. Cl.$^4$ .............................. C07C 1/20; C07C 2/00
[52] U.S. Cl. .................................... 585/403; 585/636; 585/920; 585/921
[58] Field of Search ................ 585/301, 303, 312, 314, 585/315, 316, 403, 636, 469, 640, 920, 94

[56] References Cited

U.S. PATENT DOCUMENTS

| | | | |
|---|---|---|---|
| 3,960,978 | 6/1976 | Givens et al. | 585/331 |
| 4,021,502 | 5/1977 | Plank et al. | 585/533 |
| 4,456,779 | 6/1984 | Owen et al. | 585/415 |
| 4,482,772 | 11/1984 | Tabak | 585/315 |
| 4,506,106 | 3/1985 | Hsia et al. | 585/312 |
| 4,542,252 | 9/1985 | Graziani et al. | 585/640 |
| 4,543,435 | 9/1985 | Gould et al. | 585/330 |
| 4,544,776 | 10/1985 | Osterburg et al. | 568/697 |
| 4,547,602 | 10/1985 | Tabak | 585/314 |
| 4,603,225 | 7/1986 | Colaianne et al. | 585/331 |
| 4,654,453 | 3/1987 | Tabak | 585/303 |
| 4,684,757 | 8/1987 | Audan et al. | 585/331 |
| 4,746,761 | 5/1988 | Audan et al. | 585/331 |
| 4,788,365 | 11/1988 | Harandi et al. | 585/312 |

*Primary Examiner*—Asok Pal
*Attorney, Agent, or Firm*—Alexander J. McKillop; Charles J. Speciale; Lowell G. Wise

[57] ABSTRACT

An integrated reactor system for conversion of methanol to ether-containing high octane gasoline and distillate. Methanol is converted to olefins in the presence of zeolite MTO catalyst. $C_4$ and $C_5$ olefin fraction is converted to MTBE and TAME in the presence of excess methanol and acid etherification catalyst. Unreacted methanol and hydrocarbons are passed to an olefins to gasoline and distillate oligomerization unit in conjunction with $C_3$, $C_6$ and $C_7$ olefins from the methanol to olefins unit whereby distillate and LPG products are produced. Gasoline products from the oligomerization unit are passed to the etherification unit whereby an ether-rich gasoline fraction is separated.

2 Claims, 1 Drawing Sheet

MULTISTAGE REACTOR SYSTEM FOR PRODUCTION OF FUELS

REFERENCE TO COPENDING APPLICATION

This application is a continuation-in-part of U.S. patent application Ser. No. 130,256, filed Dec. 8, 1987, now U.S. Pat. No. 4,788,365, incorporated herein by reference.

BACKGROUND OF THE INVENTION

This invention relates to a reactor system for the production of high octane gasoline and distillates from lower aliphatic oxygenates. In particular, the invention relates to an integrated plant for the conversion of methanol, dimethyl ether or the like to high octane gasoline and distillates in conjunction with the production of methyl tertiary alkyl ethers.

In recent years the petroleum industry has witnessed the development of highly effective novel processes for the synthetic production of gasoline by the conversion of methanol over zeolite type catalyst, particularly medium pore size shape selective aluminosilicate catalyst. Further technological development has broadened the range of this technology to encompass the production of olefins, distillates and aromatics, based on $C_1$ chemistry and, in particular, methanol. The ready availability of synthetic methanol from feedstocks such as natural gas, coal and wood provide, a broad basis for the production of synthetic gasoline, distillates, olefins and aromatics. Various processes in the aforenoted field of technology are described in the following U.S. patents which are incorporated herein in their entirety by reference: U.S. Pat. Nos. 3,894,107 (Butter, et al); 3,928,483; 4,025,575; 4,252,479 (Chang, et al); 4,025,572 (Lago); 4,328,384 (Daviduk, et al); 4,547,616 (Avidan, et al); 4,450,311 (Right, et al); 3,960,978 and 4,021,502 (Plank, Rosinski and Givens); 4,150,062, 4,211,640 and 4,227,992 (Garwood, et al).

Paralleling the technological development of methanol to olefins, gasoline and distillate processes has been development of processes for production of methyl tertiary alkyl ethers as octane boosters in place of conventional lead additives in gasoline. The etherification processes for the production of methyl tertiary alkyl ethers, in particular methyl tertiary butyl ether (MTBE) and methyl tertiary amyl ether (TAME) have been the focus of considerable research attention to resolve certain limitations in the etherification process with respect to the opportunity to drive the equilibrium dependent etherification reaction to completion by conducting etherification in the presence of excess methanol. It is known that recovering unreacted methanol by conventional separation and extraction techniques imposes severe economic burdens on the etherification process. Recognizing the feedstock commonality (methanol) for the synthetic production of gasoline as well as the production of methyl tertiary alkyl octane boosting ethers research workers have endeavored to combine these processes in a manner to provide a synergistically beneficial integrated process.

Accordingly, it is an object of the present invention to provide an integrated system for the production of synthetic gasoline and distillates wherein the gasoline fraction thereof is rich in octane boosting ethers.

Another object of present invention is to provide a system for the manufacture of methyl tertiary alkyl ethers in the presence of a large excess of methanol by a process reactor integration with methanol to olefins, gasoline and distillate technology.

SUMMARY OF THE INVENTION

A novel reactor system has been designed for conversion of methanol to ether-rich high octane gasoline and distillate, comprising; first reactor means for containing solid catalyst particles for the conversion of methanol to olefins; second reactor means operatively connected to said first reactor to receive a portion of effluent stream therefrom for oligomerization of olefins to distillate and gasoline; etherification reactor means for containing etherification catalyst receivably connected to said first and second reactor means and to methanol feedstream conduit whereby iso-olefins are converted to methyl tertiary alkyl ethers; fractionator means, operatively connected to said etherification reactor means and in communication with said second reactor means, for separating vapor and liquid fractions from etherification reactor effluent whereby etherification reactor vapor fraction is passed to said second reactor.

THE DRAWINGS

FIG. 1 is a process flow schematic diagram of the integrated reactor system of the present invention.

DETAILED DESCRIPTION OF THE INVENTION

Figure 1:
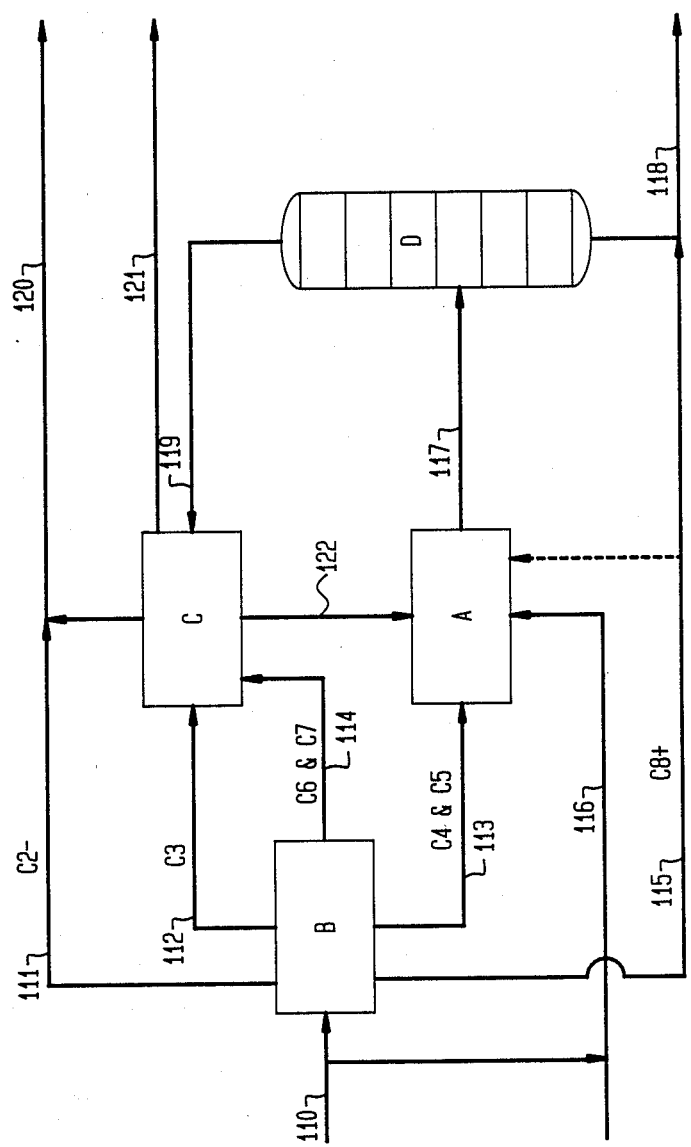

In the preferred embodiment of the instant invention the principal components of known unit operations are integrated in a manner providing a highly advantageous and surprising advancement in refinery technology leading to the production of high octane gasoline and distillate. Known processes are combined in a unique configuration that provides enhancement of the performance of component processes as well as achieving surprising advantages for the integrated process. The processes integrated include etherification to produce MTBE and TAME, the conversion of methanol to olefin, known as the MTO process and the conversion of olefins to gasoline and distillate, known as the oligomerization or MOGD process. The MTO and MOGD processes are closely related unit operations employing medium pore size shape selective zeolite type catalyst whose operating conditions are selected to shift the conversion reaction toward the production of olefins, in the case of MTO and the conversion of olefins to gasoline and distillate in the case of MOGD. These known processes are discussed further herein. However, in FIG. 1, the fully integrated process of the present invention incorporating these individual processes is presented in a schematic drawing.

Referring now to FIG. 1, the present invention involves the integration of etherification reaction unit A with methanol-to-olefins unit B and olefins to gasoline and distillate unit C. Separation unit B links the etherification process and the MOGD unit. The reaction conditions in etherification, methanol-to-olefins and olefins to gasoline and distillate processes are essentially those encompassing the range of conditions under which these known processes are conventionally conducted as described hereinafter. The various unit operations are operatively connected by fluid handling means for passing the various liquid and vapor streams from effluent fractionators to downstream reactors or product recovery.

I FIG. 1, the feedstream 110 to the MTO unit comprises light oxygenated hydrocarbons such as dimethyl ether or methanol. The feedstream, preferably methanol or dimethyl ether, is fed to the catalytic reactor of the MTO unit containing medium pore size shaped selective metallosilicate catalyst, such as aluminosilicate, preferably ZSM-5, with an average alpha value of about 1 to 15, but preferably between 3 to 8. The reactor may be a fixed or fluid bed reactor but preferably a fluid bed reactor wherein catalyst is oxidatively regenerated in a separate vessel. Conversion of methanol to olefins is achieved at temperatures of about 470° to 515° C. and pressures of about 220–350 kPa.

In the present invention the MTO unit B first effluent stream is separated by fractionation means to provide a $C_2-$ stream 111, $C_3$ stream 112, a $C_4$ and $C_5$ stream 113, $C_6$ and $C_7$ stream 114 and $C_8{}^+$ stream 115. The $C_4$ and $C_5$ stream 113 is passed to a second reactor in etherification unit A along with methanol feedstream 116 and, optionally, a portion of the $C_8{}^+$ stream. Etherification of the $C_4$ and $C_5$ stream, comprising isobutylene and isoamylene, with methanol is achieved under moderate conditions in the presence of an acid resin catalyst.

The reaction of methanol with isobutylene and isoamylenes at moderate conditions with a resin catalyst is known technology, as provided by R. W. Reynolds, et al in *The Oil and Gas Journal*, June 16, 1975, and S. Pecci and T. Floris, *Hydrocarbon Processing*, December 1977. An article entitled "MTBE and TAME-a Good Octane Boosting Combo," by J. D. Chase, et al, *The Oil and Gas Journal*, Apr. 9, 1979, pages 149–152, discusses the technology. A preferred catalyst is a bifunctional ion exchange resin which etherifies and isomerizes the reactant streams. A typical acid catalyst is Amberlyst 15 sulfonic acid resin.

Processes for producing and recovering MTBE and other methyl tertiary alkyl ethers from $C_4$–$C_7$ isolefins are known to those skilled in the art, such as disclosed in U.S. Pat. Nos. 4,544,776 (Osterburg, et al) and 4,603,225 (Colaianne, et al). Various suitable extraction and distillation techniques are known for recovering ether and hydrocarbon streams from etherification effluents.

Referring again to FIG. 1 the etherification second effluent stream 117, which comprises $C_5{}^+$ gasoline, MTBE, TAME, unreacted methanol and unreacted olefins, is passed to fractionation separator D. From the fractionation separator a bottom liquid stream 118 is separated which comprises an ether rich high octane gasoline product. The overhead vapor stream from fractionator 119, comprising unreacted methanol plus $C_4$ and $C_5$ hydrocarbons, is passed by fluid handling means to the olefins to a third reactor in gasoline and distillate (MOGD) unit C. In MOGD unit C olefins are oligomerized and methanol converted to produce gasoline, distillate, LPG and lighter hydrocarbons. The oligomerization products are separated by fractionation into an LPG and lighter stream 120, distillate stream 121, and gasoline stream 122. Gasoline stream 122 is passed to the etherification unit in conjunction with the aforenoted streams 113, 116 and, optionally, a portion of 115.

Operating details for typical MOGD units are disclosed in U.S. Pat. Nos. 4,456,779; 4,497,968 (Owen, et al) and 4,433,185 (Tabak) incorporated herein by reference.

An advantageous feature of the present invention involves the etherification of iso-olefins, such as isobutylene and isoamylene in the presence of a large excess of methanol so as to shift the equilibrium of the etherification reaction favorably toward the formation of ethers. Separation of unreacted methanol is uniquely accomplished in separator D of FIG. 1, augmented by $C_4$ and $C_5$ hydrocarbons fed to the etherification unit in stream 122. Since the fractionation of methanol in separator D occurs as an azeotrope with hydrocarbons, the presence of added hydrocarbon provides for an enhancement in methanol separation. Further, the recovery of methanol is avoided since the unreacted methanol from etherification is passed to the MOGD unit for conversion to olefins, gasoline and distillate.

The catalyst useful in the practice of the instant invention in the conversion of methanol to olefins and in the conversion of olefins to gasoline and distillate belongs to a group of related zeolites. Recent developments in zeolite technology have provided a group of medium pore siliceous materials having similar pore geometry. Most prominent among these intermediate pore sized zeolites is ZSM-5, which is usually synthesized with Bronsted active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedrally species having varying degrees of acidity. ZSM-5 crystalline structure is readily recognized by its x-ray diffraction pattern, which is described in U.S. Pat. No. 3,702,866, (Argauer, et al), incorporated by reference.

While the invention has been described by reference to particular embodiments, there is no intent to limit the inventive concept as set forth in the following claims.

We claim:

1. An integrated reactor system for conversion of oxygenated hydrocarbon to high octane gasoline and distillate fuels, comprising:
   (a) first reactor means for contacting oxygenated hydrocarbon feed with solid conversion catalyst in a conversion zone under oxygenate conversion conditions to produce a first effluent stream comprising a major portion of olefinic hydrocarbons;
   (b) fractionation means for separating said first effluent stream to provide a first $C_2-$ olefinic stream, a second $C_3$ olefinic stream, a third $C_4$ and $C_5$ olefinic stream containing iso-olefins, a fourth $C_6$–$C_7$ olefinic stream and a fifth $C_8{}^+$ olefinic stream;
   (c) fluid handling means for passing said second $C_3$ olefinic stream and said fourth $C_6$–$C_7$ olefinic stream to an olefins oligomerization zone in a second reactor;
   (d) second reactor means for converting said second and fourth streams under oligomerization conditions in contact with medium pore size shape selective zeolite catalyst, whereby $C_5{}^+$ gasoline and distillate are produced;
   (e) fractionation means for separating second reactor effluent to recover a distillate product stream, light hydrocarbon byproduct and a $C_5{}^+$ gasoline stream;
   (f) fluid handling means for passing at least a portion of said $C_5{}^+$ gasoline from fractionation means (e) and said third $C_4$–$C_5$ olefinic hydrocarbon stream from (b) in conjunction with a methanol feedstream providing a stoichiometric excess of methanol to iso-olefins to an etherification zone in a third reactor;

(g) third reactor means for converting iso-olefins contained in said $C_5+$ gasoline and said third stream in contact with an acid etherification catalyst under etherification conditions to produce a high octane ether-rich gasoline mixture;

(h) fractionation means for recovering an overhead vapor stream comprising unreacted methanol and $C_4$ and $C_5$ hydrocarbons and a liquid bottom stream comprising ether-rich gasoline; and (i) fluid handling means for passing the methanol containing vapor stream comprising unreacted methanol and $C_4$ and $C_5$ hydrocarbons to said second reactor oligomerization zone for conversion to gasoline and distillate.

2. A reactor system for conversion of methanol to ether-rich high octane gasoline and distillate, comprising in combination;

first reactor means for containing solid catalyst particles for the conversion of methanol to olefins;

second reactor means operatively connected to said first reactor to receive a portion of effluent stream therefrom for oligomerization of olefins to distillate and gasoline;

etherification reactor means for containing etherification catalyst receivably connected to said first and second reactor means and to methanol feedstream conduit whereby iso-olefins are converted to methyl tertiary alkyl ethers;

fractionator means, operatively connected to said etherification reactor means and in communication with said second reactor means, for separating vapor and liquid fractions from etherification reactor effluent whereby etherification reactor vapor fraction is passed to said second reactor.

* * * * *

UNITED STATES PATENT AND TRADEMARK OFFICE
CERTIFICATE OF CORRECTION

PATENT NO. : 4,885,421

DATED : December 5, 1989

INVENTOR(S) : Mohsen N. Harandi and Hartley Owen

It is certified that error appears in the above-identified patent and that said Letters Patent is hereby corrected as shown below:

On the title page, add the following:
--[73]Assignee: Mobil Oil Corporation--

Signed and Sealed this

Nineteenth Day of March, 1991

Attest:

HARRY F. MANBECK, JR.

*Attesting Officer*      *Commissioner of Patents and Trademarks*